(12) United States Patent
Tsuchiya et al.

(10) Patent No.: US 7,442,937 B2
(45) Date of Patent: Oct. 28, 2008

(54) RADIATION IMAGING APPARATUS AND NUCLEAR MEDICINE DIAGNOSIS APPARATUS USING THE SAME

(75) Inventors: Katsutoshi Tsuchiya, Hitachi (JP); Hiroshi Kitaguchi, Naka (JP); Yuichi Morimoto, Hitachinaka (JP); Shinya Kominami, Mito (JP); Kazuma Yokoi, Hitachi (JP); Tsuneaki Kawaguchi, Kashiwa (JP); Masatoshi Tanaka, Kashiwa (JP); Takafumi Ishitsu, Hitachi (JP)

(73) Assignee: Hitachi, Ltd., Chiyoda-Ku (JP)

( * ) Notice: Subject to any disclaimer, the term of this patent is extended or adjusted under 35 U.S.C. 154(b) by 0 days.

(21) Appl. No.: 11/822,031

(22) Filed: Jun. 29, 2007

(65) Prior Publication Data
US 2008/0029705 A1 Feb. 7, 2008

Related U.S. Application Data

(63) Continuation of application No. 11/199,262, filed on Aug. 9, 2005, now abandoned.

(30) Foreign Application Priority Data

Sep. 24, 2004 (JP) ............................. 2004-277351
Mar. 30, 2005 (JP) ............................. 2005-096672

(51) Int. Cl.
*G21K 1/02* (2006.01)
(52) U.S. Cl. .................................. 250/363.1
(58) Field of Classification Search ............ 250/363.01
See application file for complete search history.

(56) References Cited

U.S. PATENT DOCUMENTS

| | | | | |
|---|---|---|---|---|
| 5,666,395 A | * | 9/1997 | Tsukamoto et al. | 378/98.4 |
| 6,181,773 B1 | * | 1/2001 | Lee et al. | 378/155 |
| 6,252,938 B1 | * | 6/2001 | Tang | 378/154 |
| 6,366,643 B1 | * | 4/2002 | Davis et al. | 378/154 |
| 6,650,928 B1 | | 11/2003 | Gailly et al. | |
| 6,690,767 B2 | * | 2/2004 | Davis | 378/154 |
| 6,778,632 B2 | * | 8/2004 | Hoheisel et al. | 378/98.8 |

(Continued)

FOREIGN PATENT DOCUMENTS

JP 08256259 A 10/1996

(Continued)

OTHER PUBLICATIONS

Ohnishi, H., et al., "Nuclear Medicine Examination Technology, Japanese Society of Radiological Technology", Ohmsha, Ltd., Apr. 30, 2002, pp. 79-80 and pp. 76-77.

*Primary Examiner*—Christine Sung
(74) *Attorney, Agent, or Firm*—Dickstein Shapiro LLP

(57) ABSTRACT

Disclosed herein is a radiation imaging apparatus and radiation-imaging-apparatus-based nuclear medicine diagnosis apparatus having a collimator in which a plurality of rectangular through-holes are arranged in a grid pattern and separated by septa is rotated through a predetermined angle as viewed from above in relation to the layout of a plurality of rectangular detectors that are arranged in a grid pattern. The predetermined angle ranges from 20 to 70 degree and more preferably from 30 deg to 60 deg. With this configuration, the influence of sensitivity variations (moire patterns) that are included in an image picked up due to interference with a collimator when pixel type detectors are used is eliminated.

14 Claims, 14 Drawing Sheets

U.S. PATENT DOCUMENTS

| | | | |
|---|---|---|---|
| 6,993,110 B2 * | 1/2006 | Hoffman | 378/19 |
| 7,110,507 B2 * | 9/2006 | Schmitt | 378/154 |
| 2004/0251420 A1 * | 12/2004 | Sun | 250/370.09 |

FOREIGN PATENT DOCUMENTS

| | | | |
|---|---|---|---|
| JP | 09-236666 A * | | 9/1997 |
| JP | 2002-062357 A * | | 2/2002 |
| JP | 2003-038483 A * | | 2/2003 |
| JP | 2004-151089 | | 5/2004 |
| WO | WO 00/26922 A | | 5/2000 |
| WO | WO 03/017838 | | 8/2003 |

* cited by examiner

[COMPARATIVE EXAMPLE 1]

[COMPARATIVE EXAMPLE 1]

[COMPARATIVE EXAMPLE 2]

FIG. 9
[COMPARATIVE EXAMPLE 2]
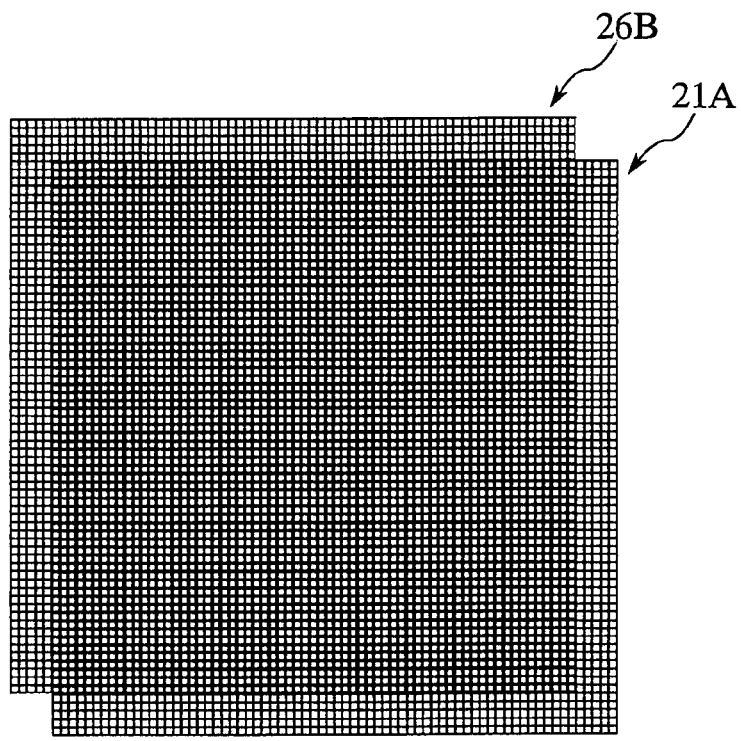
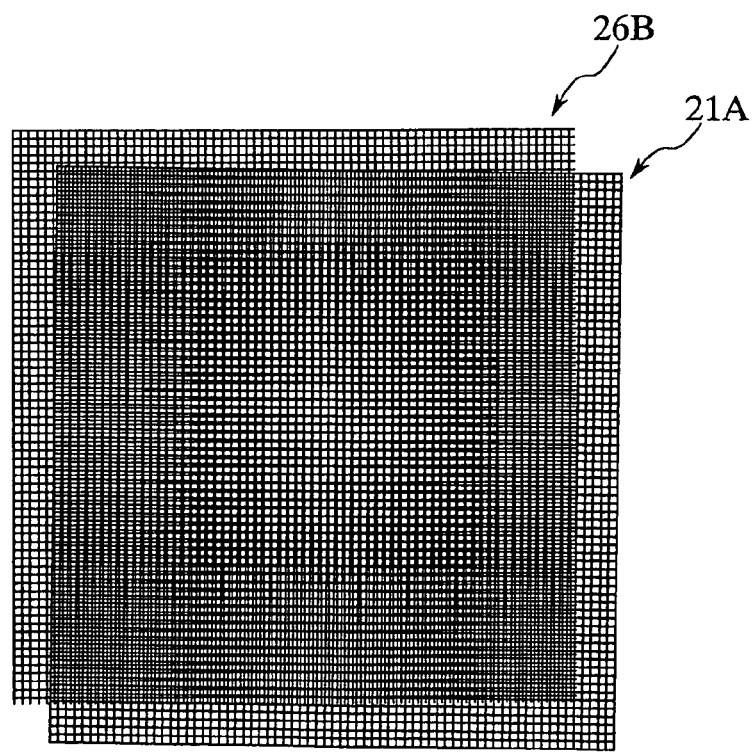

[EMBODIMENT 1]

[EMBODIMENT 2]

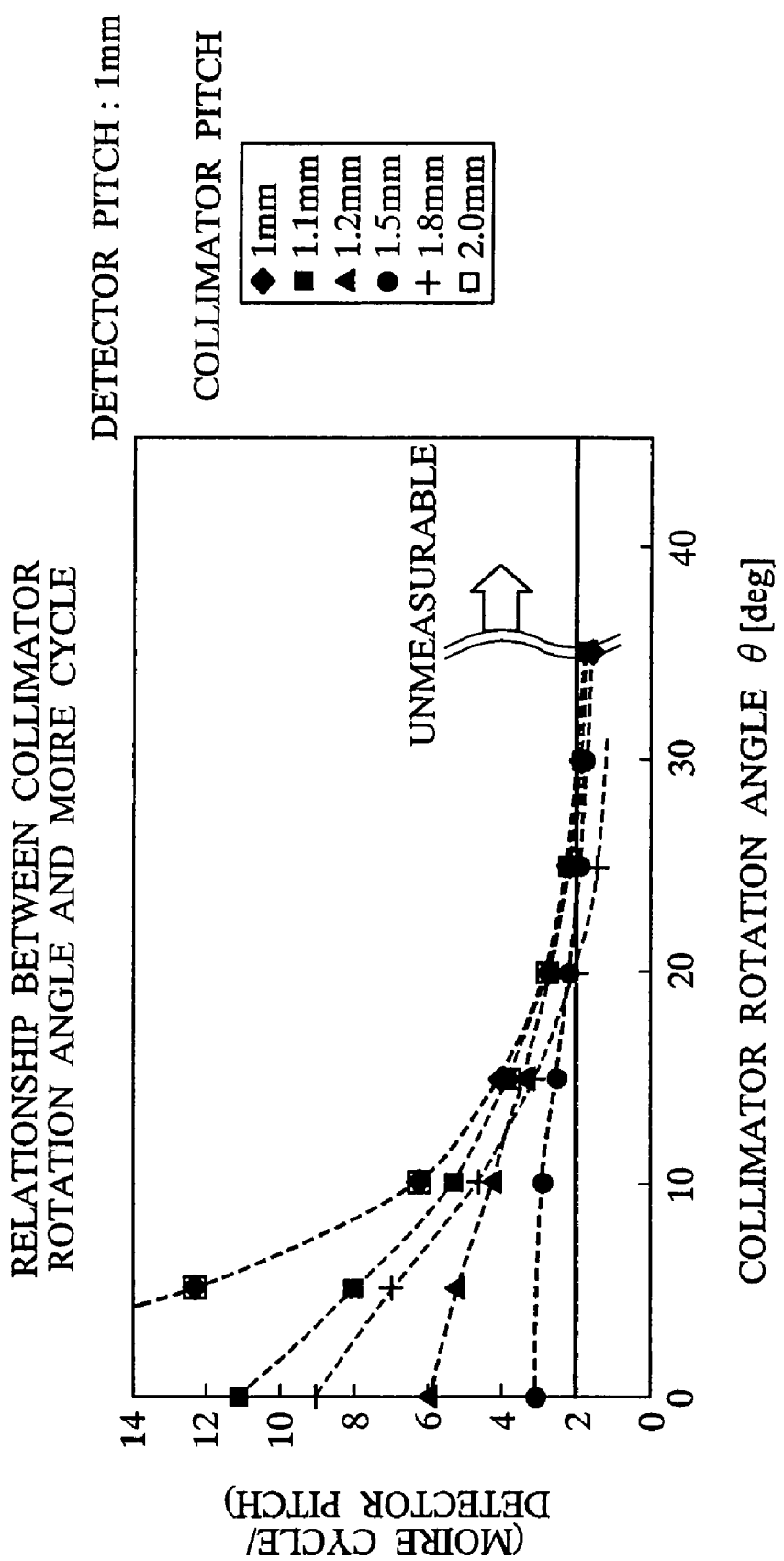

RELATIONSHIP BETWEEN COLLIMATOR
ROTATION ANGLE AND MOIRE CYCLE

HEXAGONAL
COLLIMATOR USED

NO FILTER PROCESS
PERFORMED

HEXAGONAL
COLLIMATOR USED

FILTER PROCESS
PERFORMED 45-deg ROTATED RECTANGULAR COLLIMATOR USED

NO FILTER PROCESS PERFORMED 45-deg ROTATED RECTANGULAR COLLIMATOR USED

FILTER PROCESS PERFORMED

RADIATION IMAGING APPARATUS AND NUCLEAR MEDICINE DIAGNOSIS APPARATUS USING THE SAME

CROSS-REFERENCE TO RELATED APPLICATIONS

This application is a continuation of U.S. patent application Ser. No. 11/199,262, filed on Aug. 9, 2005, now abandoned the subject matter of which is incorporated in its entirety by reference herein.

BACKGROUND OF THE INVENTION

1. Technical Field

The present invention relates to a radiation imaging apparatus that includes a pixel-type measurement system and images an incident radiation distribution, and to a nuclear medicine diagnosis apparatus that uses the radiation imaging apparatus.

2. Background Art

A gamma camera, single photon emission computed tomography (SPECT) apparatus that uses a gamma camera, or other nuclear medicine diagnosis apparatus is used as an apparatus that uses a radiation measurement device for medical purposes. Radiation detectors (hereinafter may be referred to as detectors) for use in such a nuclear medicine diagnosis apparatus are mostly a combination of a scintillator and a photomultiplier tube. For such a nuclear medicine diagnosis apparatus, a single, large crystal plate is generally used. A NaI (T1) scintillator is widely used for the gamma camera and SPECT apparatus.

FIG. 13 schematically illustrates the configuration of a scintillator-based gamma camera. A single plate of scintillator 201, which comprises a relatively large single crystal, is a detector that makes use of a phenomenon in which fluorescence is generated when radiation energy is absorbed subsequently to radiation incidence on a particular substance. The generated feeble light is amplified by a plurality of photomultiplier tubes 203 to achieve radiation detection. For radiation position measurement purposes, the output signals generated from the plurality of photomultiplier tubes 203 are subjected to gravity center computation to determine a radiation reaction position.

To project a gamma ray generation position onto an image pickup surface of the detector, a collimator 206 for controlling the angle of radiation incidence is positioned in front of the scintillator 201. At present, the collimator 206 is generally made of lead that has an infinite number of hexagonal through-holes. The through-hole diameter approximately ranges from 1 mm to 3 mm. The through-hole length approximately ranges from 40 mm to 60 mm. The septa among the through-holes approximately range from 0.2 mm to 3 mm. Hexagonal through-holes are used because they provide the highest aperture ratio, are easy to fabricate, and exhibit high strength. In FIG. 13, the reference numeral 202 denotes a light guide; 204, a measurement circuit; and 205, a measurement circuit retention board.

In recent years, individual pixel type detectors, which acquire position signals in the unit of a small detector, that is, on an individual pixel basis, have been developed, including a gamma camera in which a CsI (T1)-based pixel type scintillator and photodiode are used (Nuclear Medicine Examination Technology, Japanese Society of Radiological Technology, Ohmsha, pp. 79-80) and a semiconductor detector for directly converting radiation into electrical signals (Nuclear Medicine Examination Technology, Japanese Society of Radiological Technology, Ohmsha, pp. 76-77). Detectors that determine the radiation reaction position by means of aforementioned gravity center computation measure one gamma ray by using a plurality of photomultiplier tubes to capture scintillator-generated light as a spread of light. Therefore, it can be said that the detectors make spatially continuous measurements, that is, analog measurements. On the other hand, it can be said that pixel-type detectors, which make measurements on an individual pixel basis, measure one gamma ray by making spatially discrete measurements, that is, spatially digital measurements.

One measurement unit, that is, the radiation incidence cross section of a pixel, of the above apparatuses is generally rectangular. The collimator having hexagonal through-holes is not suitable for the above apparatuses. The reason is that moire patterns arise although they do not arise with the use of a conventional scintillator, which comprises a single crystal. The generation of moire patterns is a problem in which a plurality of periodical sensitivity variations occur on an image when the periodical shade changes of septa interfere with each pixel due to the difference between the detector pitch and through-hole pitch and anisotropy.

One solution to avoid moire patterns is to use a collimator whose hole diameter is smaller than half the pixel size. When the collimator through-hole is small, the following advantages are provided. When the collimator is shifted horizontally in relation to the detectors, a septum positioned over one detector is partly positioned outside the detector. However, another septum, which has virtually the same area and was positioned outside the detector, is now positioned over the detector. As a result, the septum area over the detector does not significantly change even when the collimator is shifted. Consequently, the detector sensitivity does not significantly change. In other words, the resulting image remains almost unchanged because pixels are almost uniform in sensitivity even when the collimator is moved forward, rearward, leftward, or rightward, rotated, or otherwise shifted. The smaller the collimator through-holes in relation to the detectors, the greater the produced effect.

However, when the pixel size is 1 mm or larger, the above solution does not work due to the manufacturing limitation imposed on the collimator hole diameter. As a result, moire patterns cannot be avoided.

Another solution is to use a matched collimator, which has rectangular holes that match the pixel size. Since the sensitivity loss due to the septa 28 is minimized for the pixel-type detectors, it is said that the use of a matched collimator is ideal. However, when the current lead-based collimator is used, it is difficult to maintain the manufacturing accuracy in order to provide the advantages of the matched collimator. The reason is that lead is relatively soft and likely to deform. Further, if, for instance, the collimator mounting position is slightly shifted from normal, a great sensitivity variation may arise. The collimator can be made of relatively hard tungsten in order to maintain the required manufacturing accuracy. Such a solution may work with collimators for use in a small-size gamma camera, but does not provide a practical solution for collimators for use in a normal gamma camera, SPECT, or the like in terms of cost.

Further, the gamma camera rotates or moves in a complicated manner during an image pickup operation. During such a movement, the collimator may deviate from a specified position.

Even while the gamma camera is at a standstill for a long period of time, the collimator may gradually deviate from a specified position due to its weight.

When displaced, the collimator incurs moire patterns no matter whether a matched collimator is used.

SUMMARY OF THE INVENTION

It is an object of the present invention to provide a radiation imaging apparatus and nuclear medicine diagnosis apparatus that have the aforementioned pixel type measurement system and are capable of avoiding moire patterns, which may be generated during the use of the aforementioned hexagonal collimator or matched collimator.

In accomplishing the above object, according to one aspect of the present invention, there is provided a radiation imaging apparatus comprising a plurality of rectangular detectors that are arranged in a grid pattern; a radiation measurement circuit for reading detector signals; and a collimator in which a plurality of rectangular through-holes are arranged in a grid pattern and separated by septa. The radiation imaging apparatus uses the collimator to control the angle of radiation incidence and images radiation incidence position information on an individual rectangular detector basis. The collimator is rotated through a predetermined angle in relation to the layout of the detectors as viewed from above.

According to another aspect of the present invention, there is provided the radiation imaging apparatus, wherein the predetermined angle ranges from 20 deg to 70 deg and more preferably from 30 deg to 60 deg.

According to another aspect of the present invention, there is provided a nuclear medicine diagnosis apparatus that uses the radiation imaging apparatus.

According to still another aspect of the present invention, there is provided a radiation imaging apparatus comprising a plurality of pixel type detectors for acquiring radiation incidence position information in accordance with image pixels that are arranged in a grid pattern; a radiation measurement circuit for reading detection signals from the detectors, and a collimator in which a plurality of rectangular through-holes are arranged in a grid pattern and separated by septa. The collimator is rotated through a predetermined angle in relation to the grid layout of the detectors as viewed from above.

When the above configuration is employed, it is possible to avoid moire patterns that are fatal to the operation performed to image a radiation distribution (radiation source position) with pixel type detectors. Further, low-cost lead may be used for collimator manufacture because the required manufacturing accuracy and mounting accuracy are not high. As a result, the apparatus cost can be minimized.

BRIEF DESCRIPTION OF THE DRAWINGS

FIG. 4A shows the top surface of the set of pixel type detectors. FIG. 4B shows the bottom surface of the set of pixel type detectors;

FIG. 9 relates to the second comparative example and schematically shows a moire pattern that is generated when a combination of a matched collimator and pixel detectors is viewed from above. The upper drawing illustrates a situation where the collimator is horizontally shifted in relation to the detectors. The lower drawing illustrates a situation where the collimator is horizontally shifted in relation to the detectors and slightly rotated as viewed from above;

FIG. 12 illustrates the relationship between a collimator rotation angle and moire cycle;

FIG. 15A illustrates a case where raw data is used. FIG. 15B shows a case where a 3×3 weighted smoothing filter is used;

FIG. 16A illustrates a case where raw data is used. FIG. 16B shows a case where a 3×3 weighted smoothing filter is used.

DETAILED DESCRIPTION OF THE PREFERRED EMBODIMENTS

An embodiment of the present invention will now be described with reference to the accompanying drawings. In the following description, the terms "detector" and "detector array" are used. The detector corresponds to a rectangular pixel, whereas the detector array denotes a set of detectors that are arranged in a grid pattern.

Figure 1:
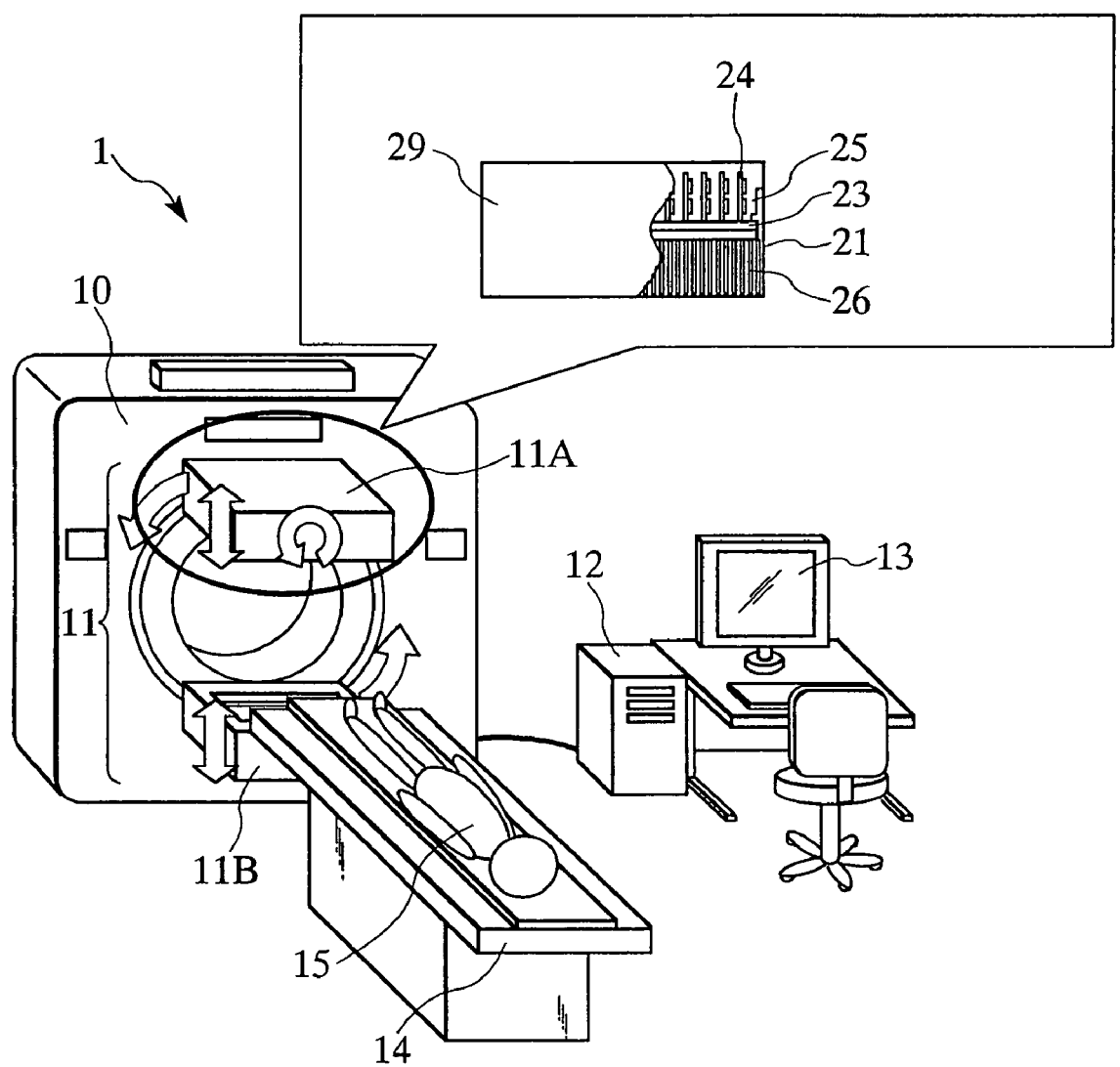
FIG. 1 illustrates a SPECT apparatus (gamma camera) according to one embodiment of the present invention.

As shown in FIG. 1, a SPECT apparatus 1 includes a gantry 10, cameras (image pickup devices) 11A, 11B, a data processing device 12, and a display device 13. A radiopharmaceutical, such as a pharmaceutical containing $^{99m}$Tc having a half-life of 6 hours, is administered to an examinee 15. Gamma rays emitted from $^{99m}$TC in the body of the examinee on a bed 14 are detected with the cameras 11, which are supported by the gantry 10, to obtain a tomogram.

The cameras 11 include a collimator 26 and a large number of detectors 21, which comprise a semiconductor device. The collimator 26 selects gamma rays emitted from the body of the examinee 15 so that only gamma rays oriented in a certain direction pass through. Gamma rays passing through the collimator 26 are detected by the detectors 21. The cameras 11 include an ASIC (application-specific integrated circuit) 25 for measuring a gamma ray detection signal. The gamma ray detection signal is delivered to the ASIC 25 via a detector circuit board 23 and an ASIC circuit board 24 for the purpose of inputting the ID of a detector 21 that has detected a gamma ray, the pulse height value of the detected gamma ray, and the gamma ray detection time. The components are enclosed within a light/gamma ray/electromagnetic shield 29, which is a part of the cameras 11, made of iron, lead, and the like, and used to block light, gamma rays, and electromagnetic waves. The data processing device 12 includes a storage device and a tomographic information creation device (not shown). The data processing device 12 acquires packet data, which includes the pulse height value of a measured gamma ray, detection time data, and detector (channel) ID, generates a planar image or generates tomogram information by converting the packet data into sinogram data, and displays the resultant image on the display device 13.

The cameras 11 can be moved in the radial direction or circumferential direction of the gantry 10. The cameras 11 pick up an image while moving along the contour of the examinee 15. The cameras 11 can also rotate around a gantry mount. When the two cameras 11A, 11B are fixed side by side, it is possible to obtain a STATIC image. In this manner, the radiopharmaceutical accumulated, for instance, on a tumor in the body of the examinee 15 is imaged to determine the location of the tumor.

Detector and Collimator

Characteristic portions of the present embodiment of the present invention will now be described.

Figure 2:
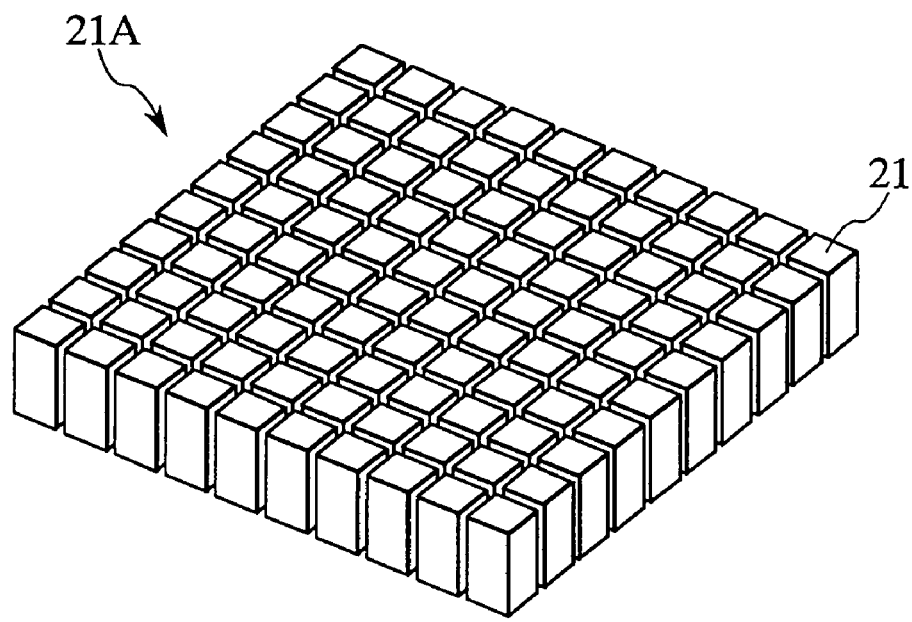
FIG. 2 illustrates a set of pixel type detectors according to one embodiment of the present invention.
Figure 3:
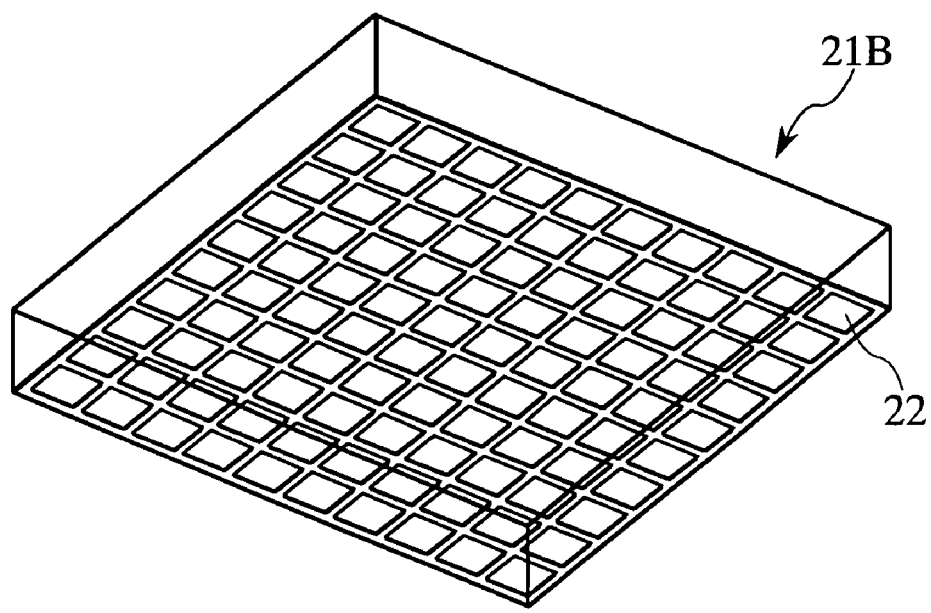
FIG. 3 illustrates another set of pixel type detectors.
Figure 4A:
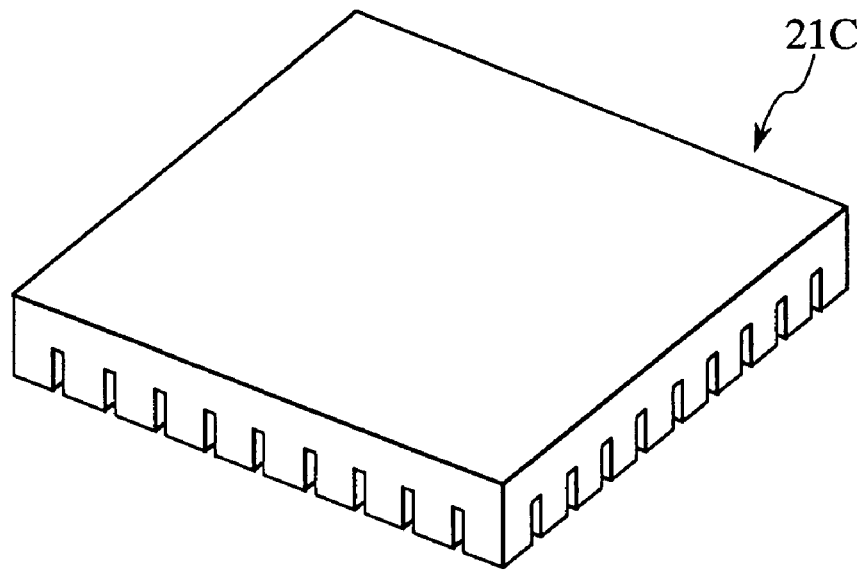
FIGS. 4A and 4B illustrate another set of pixel type detectors.
Figure 4B:
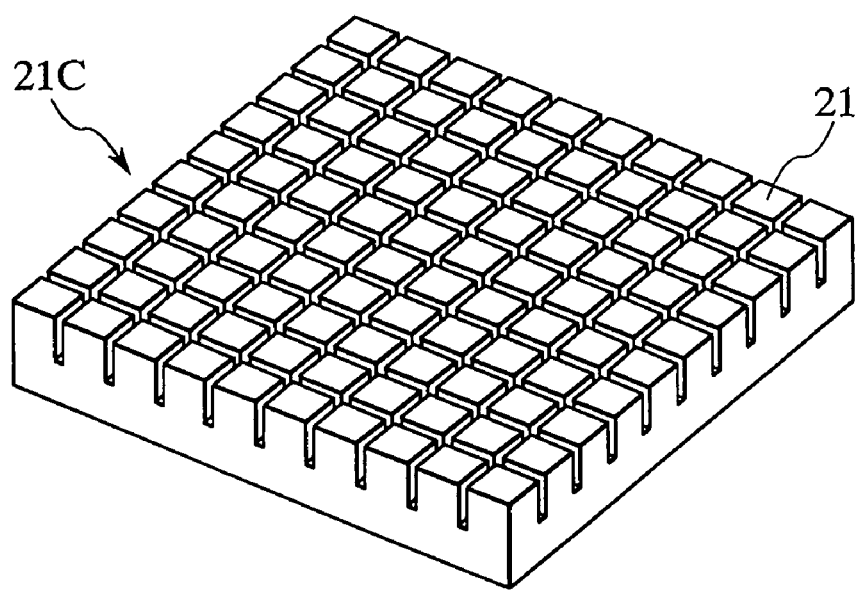
Figure 13:
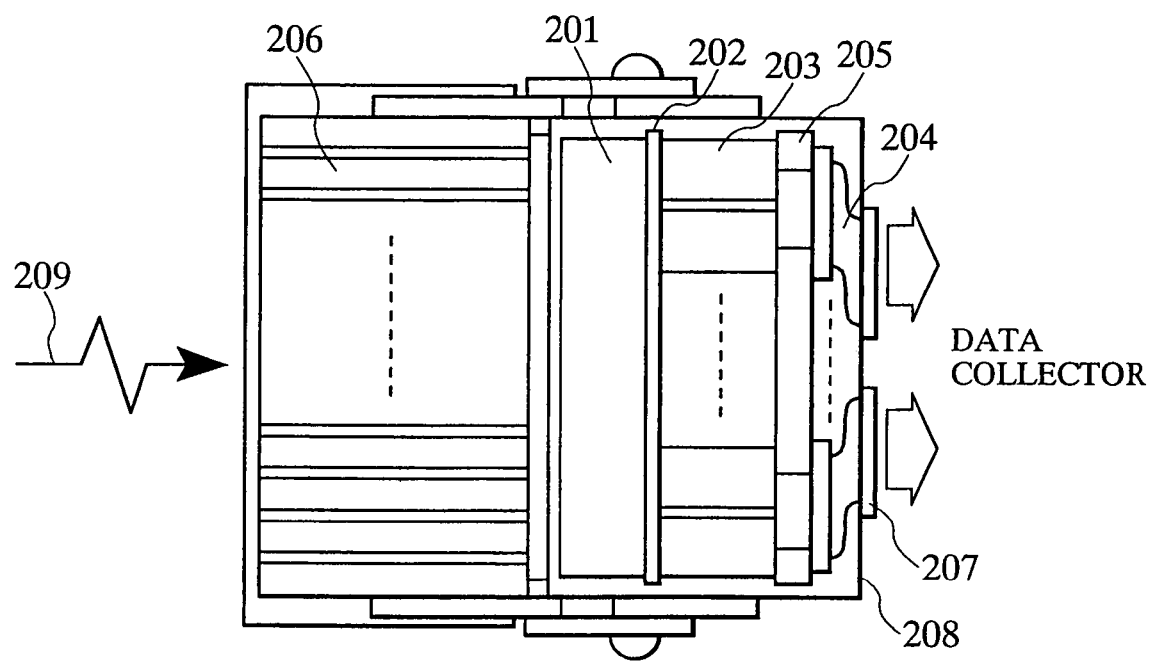
FIG. 13 schematically shows the configuration of a scintillator-based gamma camera.

As indicated in FIG. 2, the detectors 21 for use in a camera 11 are individually provided for pixels as a rectangular parallelepiped having upper and lower rectangular surfaces. A large number of detectors 21 are arranged in a grid pattern to form a detector array 21A. In marked contrast to the use of a scintillator, which comprises one big crystal as indicated in FIG. 13, detection signals are collected by individual detectors 21, that is, on an individual pixel basis. The structure of the detector array 21A need not be divisible into individual pixels. Alternatively, the structure may be such that electrodes are provided for individual pixels as indicated in FIG. 3. Another alternative structure may also be employed so that a detector array 21C comprises detectors 21 that are separated by dicing as indicated in FIGS. 4A and 4B. It goes without saying that a scintillator may be separated into individual pixels to form a number of detectors 21. In the present embodiment, the term "grid pattern" means that vertically arranged detectors 21 and horizontally arranged detectors 21, which constitute detector array 21A, 21B, or 21C, are orthogonal with each other as shown in FIGS. 2, 3, 4A, and 4B.

Figure 5:
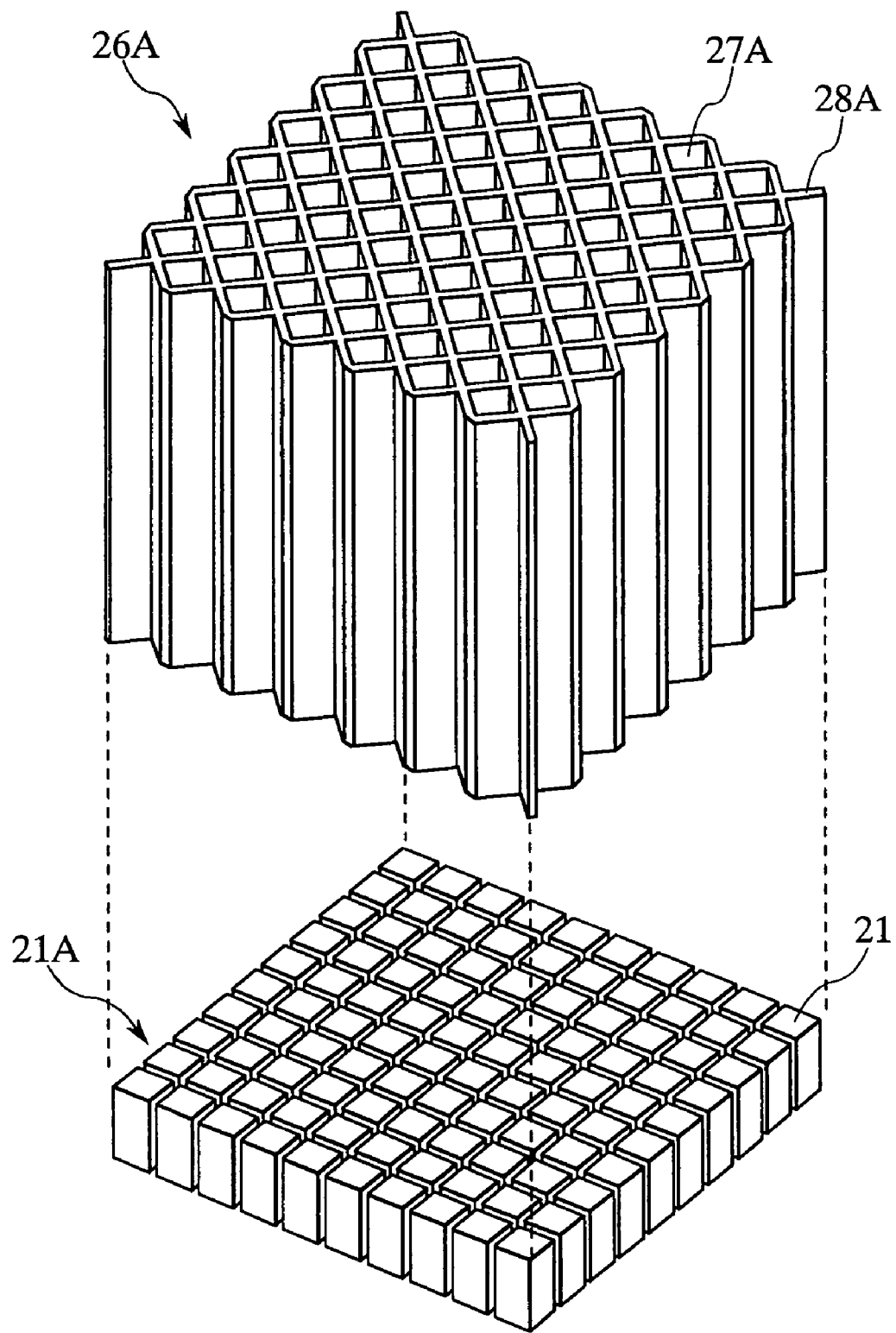
FIG. 5 illustrates a collimator and detectors according to one embodiment of the present invention.

The collimator 26A used in the present embodiment is made of lead. As shown in FIG. 5, the collimator 26A has rectangular through-holes 27A, which are arranged in a grid pattern. The through-holes 27A are separated from each other by septa. As is obvious from FIG. 5, there is a predetermined rotation angle (angle of cut) between the through-holes 27A arranged within the collimator 26A and the detectors 21 arranged within the detector array 21A when they are viewed from above. Typically, the predetermined rotation angle is 45 deg. As is the case with the detector array 21A, the term "grid pattern" means that crossing lines of through-holes 27A are orthogonal with each other.

The operations and advantages of the present embodiment, in which the collimator is rotated through a predetermined angle in relation to the layout of the detectors as viewed from above, will now be described with reference to comparative examples.

Comparative Example 1

Figure 6:
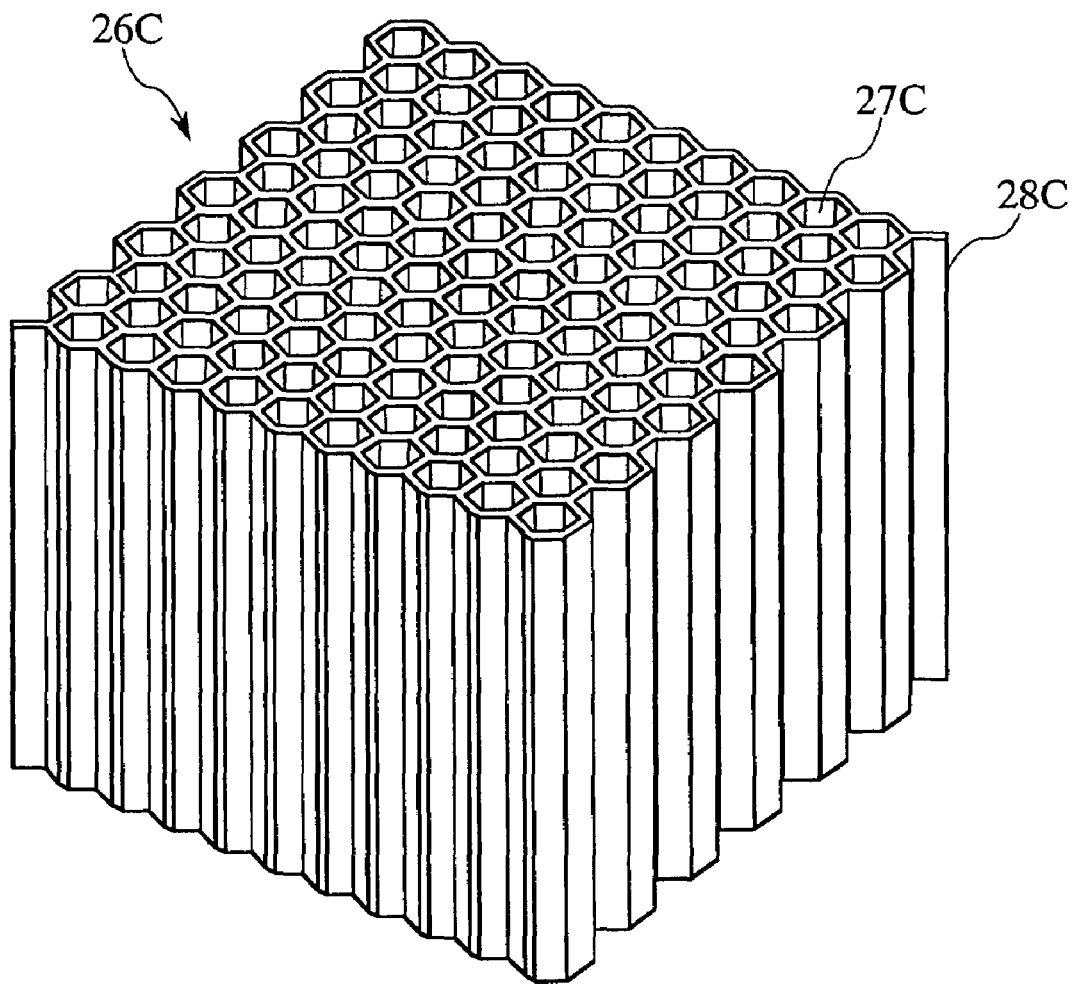
FIG. 6 shows a collimator (hexagonal holes) as a first comparative example.

FIG. 6 is furnished as a first comparative example. It is a perspective view illustrating a collimator that has hexagonal, honeycomb through-holes. This collimator 26C is made of lead. The hexagonal through-holes 27C are separated from each other by septa 28C. In the SPECT apparatus (gamma camera) 1, a collimator 26 having hexagonal through-holes as shown in FIG. 6 were formerly used (see FIG. 13). In recent years, however, a new problem has occurred due to the development of a pixel type scintillator and semiconductor detector, which detect gamma rays in the unit of a pixel. More specifically, sensitivity variations are caused by the shades of the collimator septa 28 due to the use of a spatially digitized detector system so that moire patterns appear on an image picked up.

When a photomultiplier tube based conventional technology was used, no moire-related problem occurred. The through-holes 27 of the collimator 26 are far smaller than the photomultiplier tubes 203 (see FIG. 13). Even if the collimator 26 is displaced in a situation where the aforementioned collimator hole diameter is smaller than the pixel size, the septa 28 having virtually the same area as the septa 28 placed outside a photomultiplier tube 203 is placed over a photomultiplier tube 203. Therefore, the photomultiplier tube sensitivity does not significantly change. In other words, the septa 28 do not significantly affect the photomultiplier tube sensitivity. Further, since one gamma ray is dispersed by a plurality of photomultiplier tubes 203 for measurement purposes, the septa exercise averaged influence. Consequently, the moire phenomenon does not become obvious. However, when a pixel type detector is used so that the diameter of the through-holes 27 of the collimator 26 is close to the size of the detector 21, great influence is exercised by moire patterns. Further, detection counting is performed for each pixel. Therefore, the sensitivity differences among the detectors 21 directly affect the image. As described later, the shades of the septa 28 of the collimator 26 vary from one location to another and produce great sensitivity differences.

Figure 7:
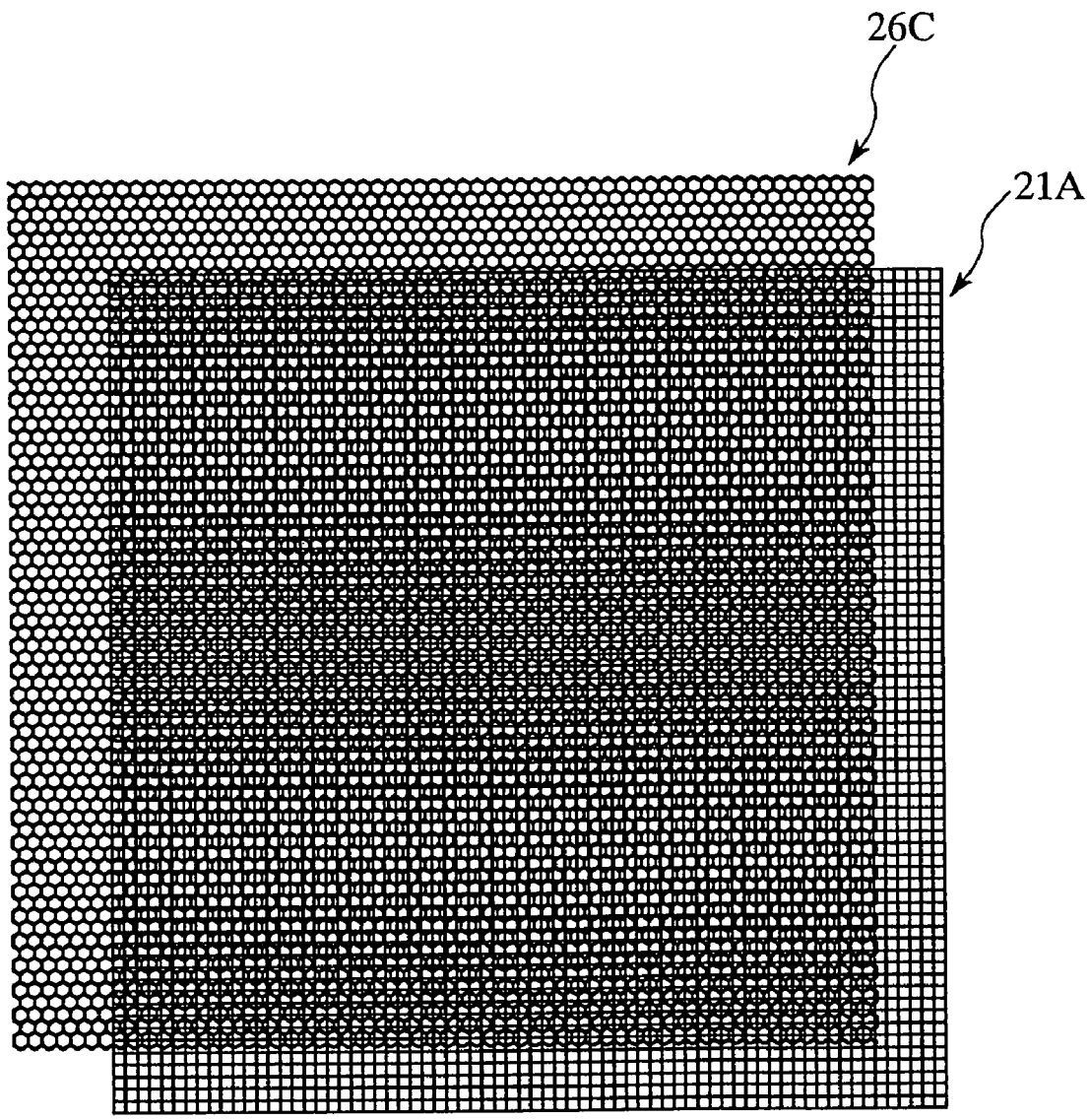
FIG. 7 relates to the first comparative example and schematically shows a moire pattern that is generated when a combination of a hexagonal collimator and pixel detectors is viewed from above.

FIG. 7 is furnished as the first comparative example to illustrate moire patterns that are generated when the collimator shown in FIG. 6 is used with the detectors shown in FIG. 2. As indicated in FIG. 7, when the collimator 26C having hexagonal through-holes 27C as shown in FIG. 6 is used with the detectors 21 (detector array 21A) shown in FIG. 2, moire patterns are generated if uniform gamma rays are emitted from a planar radiation source. In the subsequent figures, moire patterns are represented in terms of image density variation. More specifically, a dark area is a place where there are many pixels (or detectors 21) whose sensitivities are significantly lowered, whereas a light area is a place where there are many pixels whose sensitivities have insignificantly varied from normal. In FIG. 7, moire patterns are represented by lines (lines corresponding to the septum thickness and lines corresponding to a gap between the detectors) that have a certain thickness and overlap. However, the same density differences are found in an actual image that is indicated by the densities of individual pixels (the number of gamma rays detected by each pixel). If moire patterns constantly appear at the same locations, it is possible to make corrections to obtain an image that is close to a correct image.

However, (see FIG. 1), the moire patterns also depend on the depth of a diseased part that is to be imaged. The through-holes 27 of the collimator 26 have a certain length. Therefore, when a radiation source is positioned near the collimator 26, only gamma rays emitted from a narrow region can pass through the through-holes 27. If, on the other hand, the radiation source is positioned far from the collimator 26, gamma rays emitted from a wide region can pass through the through-holes 27. In reality, there is a certain gap between the detectors 21 and collimator 26. Therefore, the gamma rays emitted from the wide region are not only incident on the detectors 21 that are directly below the through-holes 27, but also incident on the neighboring detectors 21. It means that the shades of the septa 28 not only affect the detectors 21 positioned directly below the through-holes but also affect the neighboring detectors 21. Therefore, individual detector sensitivities vary depending on the depth of the diseased part so that the moire patterns vary. Further, the patterns vary when a slight positional change occurs due, for instance, to collimator replacement or the cameras 11 are rotated to slightly change the position of the collimator 26. Since these factors affect in a complicated manner, it is very difficult to make proper corrections at an image processing stage.

Comparative Example 2

Figure 8:
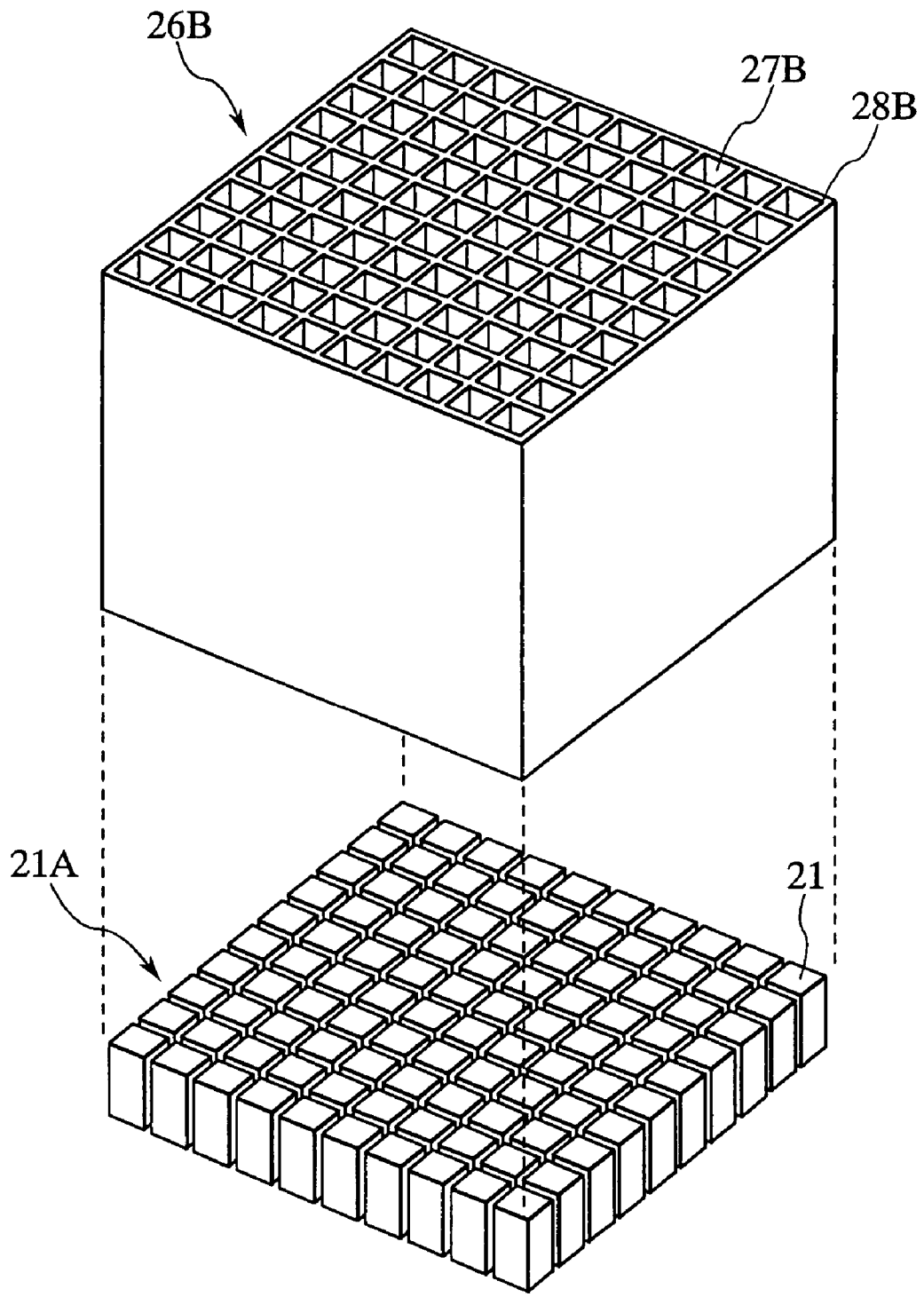
FIG. 8 shows a matched collimator as a second comparative example.

FIG. 8 is furnished as a second comparative example. It illustrates a matched collimator, which matches the layout of detectors. It is said that a matched collimator 26B should be used to avoid moire patterns. The matched collimator 26B is such that the positions of the through-holes 27B of the collimator match the positions of the detectors 21 as indicated in FIG. 8. As described earlier, each of the detectors 21 according to the present embodiment is a rectangular parallelepiped having a rectangular upper surface. These detectors 21 are arranged in a grid pattern to form the detector array 21A. The matched collimator 26B includes rectangular through-holes 27B, which are separated by septa 28B. The through-holes 27B are arranged in a grid pattern to match the layout of the detectors 21 within the detector array 21A. The through-holes 27B are oriented in the same direction as the detectors 21 as viewed from above (rotation angle=0 deg). The size of each through-hole 27B is nearly the same as that of the top surface of a detector 21. However, when the pixel size becomes smaller, it is difficult to accurately align the detectors 21 with the through-holes 27B of the matched collimator 26B. Further, it is difficult to maintain the manufacturing accuracy required for the matched collimator 26B.

Further, if the matched collimator 26B is displaced, great sensitivity differences arise. FIG. 9 illustrates moire patterns that are generated when the matched collimator is displaced. The upper drawing in FIG. 9 illustrates a situation where the matched collimator 26B is displaced in parallel with the detector array 21A. The lower drawing in FIG. 9 illustrates a situation where the matched collimator 26B is displaced in parallel with the detector array 21A and then rotated. When the matched collimator 26B is displaced in parallel with the detector array 21A, the septa 28B of the matched collimator 26B are uniformly placed over the detectors in the detector array 21A. Therefore, the overall sensitivity is greatly lowered while the sensitivity provided by a perfect match is 100%. When parallel displacement and rotary displacement both occur, great moire patterns are generated. In the SPECT apparatus 1 (see FIG. 1), which includes the lead collimator 26 that is 50 cm square and approximately 100 kg in weight, the cameras 11 rotate and the collimator 26 bends or becomes displaced. Therefore, it is extremely difficult to achieve proper positioning in any state. These problems can be solved by using a collimator 26 that is made of tungsten instead of lead. However, the use of tungsten raises the production cost and is not practical except for collimator use with a small camera. As described above, the use of pixel type detectors 21 and the moire-related problem are unavoidable.

Embodiments

The practical collimator 26 should be manufactured at a low cost and constantly achieve the same image quality without significantly varying the sensitivity from one pixel to another, and is acceptable even if does not exhibit high manufacturing accuracy and mounting accuracy. Alternatively, the employed image pickup system, which includes the detectors 21, should meet the above requirements.

In the embodiments, therefore, the collimator is provided with rectangular through-holes. The layout of the through-holes is rotated through a predetermined angle in relation to the layout of the detectors within the detector array as viewed from above.

Figure 10A:
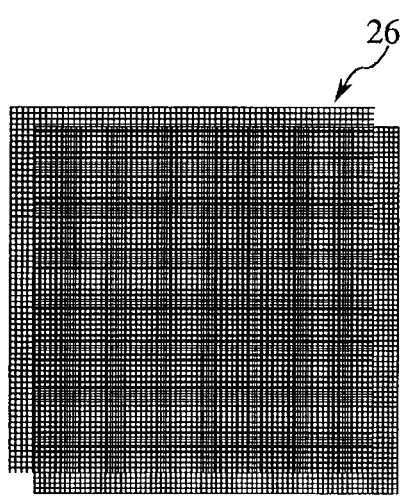
FIGS. 10A to 10D relate to a first embodiment and schematically shows a moire pattern that is generated when a combination of a collimator and pixel detectors is rotated through a predetermined angle as viewed from above.
Figure 10B:
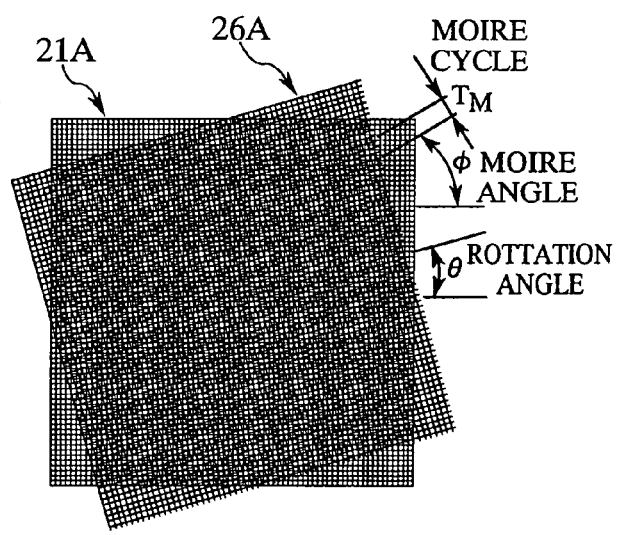
Figure 10C:
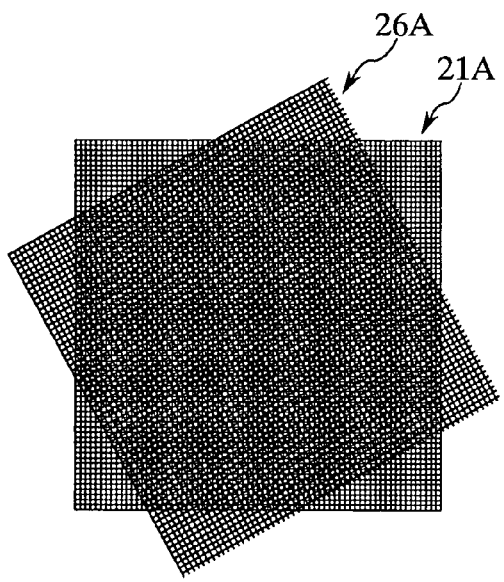
Figure 10D:
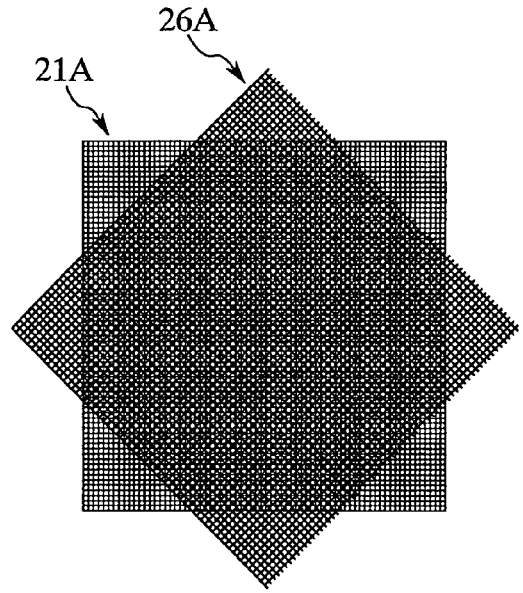
Figure 11A:
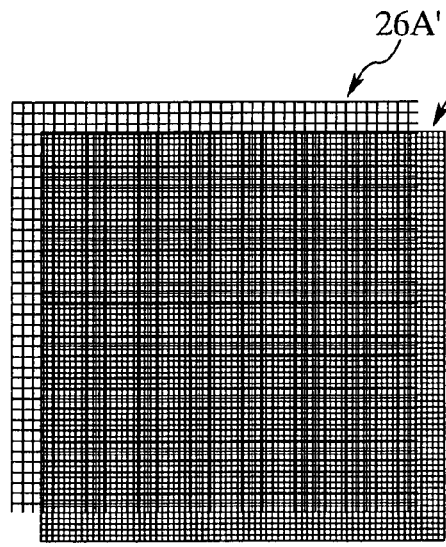
FIGS. 11A to 11D relate to a second embodiment and schematically shows a moire pattern that is generated when a combination of a collimator and pixel detectors is rotated through a predetermined angle as viewed from above.
Figure 11B:
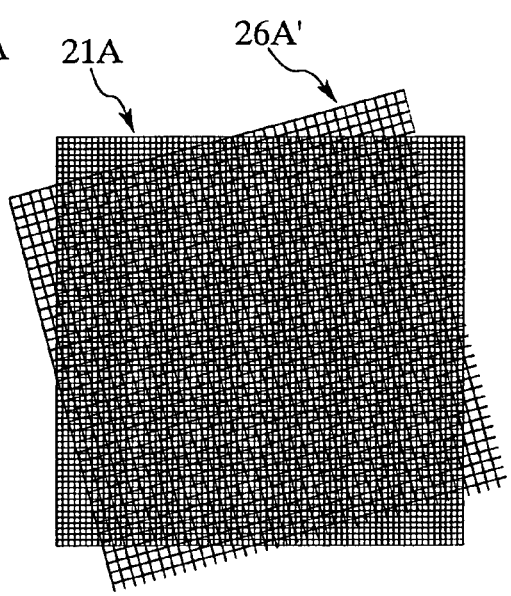
Figure 11C:
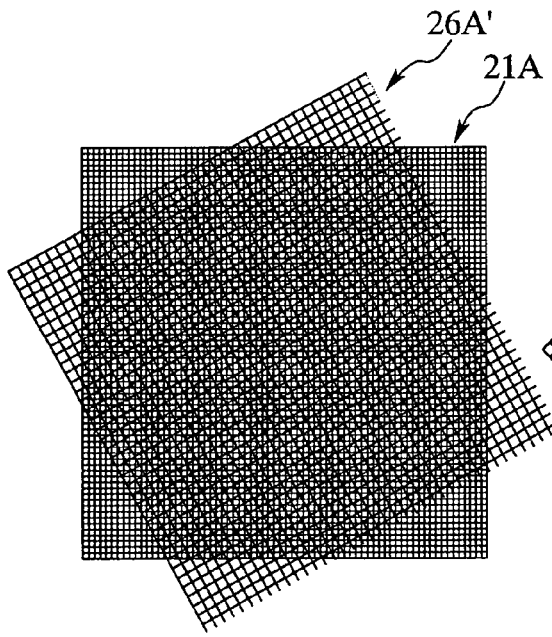
Figure 11D:
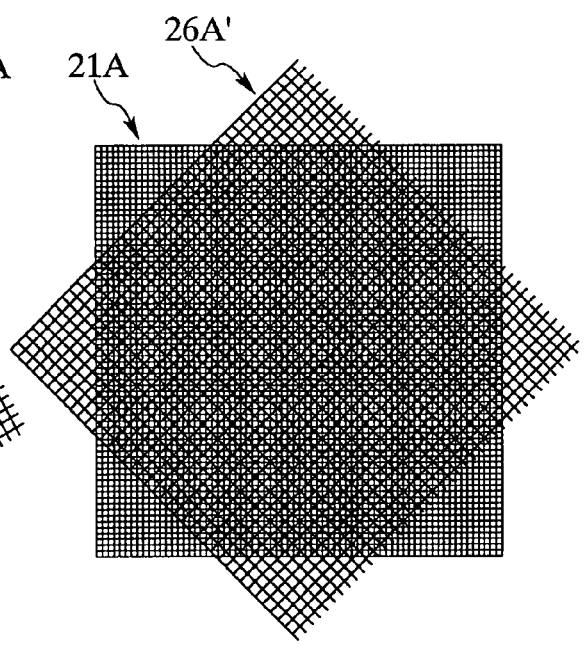

FIGS. 10A to 10D (first embodiment) and FIGS. 11A to 11D (second embodiment) indicate moire patterns that are generated while the rotation angle varies. These figures are obtained when the detectors and collimator are viewed from above. FIGS. 10A and 11A present views prevailing when the rotation angle is 0 deg. FIGS. 10B and 11B present views prevailing when the rotation angle is 15 deg. FIGS. 10C and 11C present views prevailing when the rotation angle is 30 deg. FIGS. 10D and 11D present views prevailing when the rotation angle is 45 deg. The ratio between the collimator through-hole pitch and detector pitch is 1.0 for the matched collimator, 1.1 in FIGS. 11A to 11D, and 1.8 in FIG. 12.

When the collimator is rotated through 30 deg or more, almost no moire patterns are visible in FIGS. 10A to 10D, which indicate the first embodiment, and in FIGS. 11A to 11D, which indicate the second embodiment. This moire reduction effect is similarly produced when the position of the collimator 26A is slightly changed by rotation or parallel displacement. When the through-holes 27A of the collimator 16A are rectangular with the through-hole layout direction rotationally displaced from the pixel layout direction as described above, it is possible to avoid moire patterns. The rotation angle should range from 20 to 70 degree and more preferably from 30 deg to 60 deg.

FIG. 12 (see FIGS. 10A to 10D and 11A to 11D as needed) indicates that a rotation angle of 30 deg is an angle at which the moire cycle/detector pitch is 2.0 or smaller for all collimator pitches according to the present embodiment. In other words, when the rotation angle is 30 deg or greater, moire patterns disappear at all collimator pitches according to the present embodiment. Since symmetry is achieved at a rotation angle of 45 deg, moire patterns disappear at all collimator pitches according to the present embodiment when the rotation angle is 60 deg or smaller. The reason why moire patterns disappear when the moire cycle/detector pitch is 2.0 or smaller will be described later in detail.

When the rotation angle is 20 deg or greater, it can be expected that the moire reduction effect is produced. Satisfactory results are obtained particularly when the collimator pitch is 1.5 mm or 1.8 mm. When the rotation angle is smaller than 20 deg, the influence of moire patterns greatly increases. As regards the relationship between the moire effect and rotation angle, symmetry is achieved at a rotation angle of 45 deg. Therefore, when the rotation angle is 70 deg or smaller, it can be expected that the moire reduction effect is produced. Satisfactory results are obtained particularly when the collimator pitch is 1.5 mm or 1.8 mm. When the rotation angle is 70 deg or greater, the influence of moire patterns greatly increases.

It is possible to sufficiently avoid moire patterns at a rotation angle of 20 deg by selecting an appropriate collimator pitch no matter whether it is indicated in FIG. 12.

FIG. 12 uses the ratio between the detector pitch and collimator hole pitch as a parameter and shows the measured ratio between the detector pitch and the moire cycle $T_M$ for the rotation angle θ of the collimator 26. The moire cycle $T_M$ represents the distance between the darkest spot of a moire pattern and the darkest spot of a neighboring moire pattern (or the distance between the lightest spot of a moire pattern and the lightest spot of a neighboring moire pattern). Since moire patterns at rotation angles of 45 deg or greater are the same as for (90−θ), the maximum rotation angle shown in FIG. 12 is 45 deg. Further, when the collimator pitch is more than twice the detector pitch, many pixels are not shaded by the septa 28. Therefore, the shades of the septa 28 are directly projected onto the pixels so that no conspicuous moire patterns are generated. Moire patterns are conspicuous only when the detector pitch is close to the collimator pitch. That is why the maximum collimator pitch shown in FIG. 12 is two times the detector pitch. As indicated in FIGS. 10A to 10D and 11A to 11D, virtually no moire patterns are visible when the moire cycle $T_M$ (see FIG. 10B) is not more than two times the detector pitch, that is, when the rotation angle is 30 deg or greater. When the rotation angle is 35 deg or greater, no measured data is indicated in FIG. 12 because the moire cycle $T_M$ could not be measured. To be precise, almost no moire patterns are generated when $T_M \sin \phi$ and $T_M \cos \phi$ are not more than two times the detector pitch $p_D$, where $T_M$ is the moire cycle and φ is a moire angle (slightly different from the actual rotation angle θ), which is formed between a moire pattern and the detector 21. The reason is that the minimum cycle for digital imaging is 2 pixels (that is, when white and black are adjacent to each other). Moire patterns cannot be recognized when the moire cycle $T_M$ for projection onto to the pixel layout is 2 pixels, that is, not more than two times the detector pitch $p_D$.

However, moire disappearance is one thing and detector sensitivity uniforming is another. When the collimator pitch is relatively great, the whole area of a pixel is positioned within a through-hole of the collimator 26A' as indicated in FIGS. 11A to 11D. Therefore, a pixel having the maximum sensitivity exists. Meanwhile, an intersection of septa 28A may overlap a detector 21 for one pixel so that the sensitivity is minimized. In such an instance, however, there are no great periodic sensitivity differences but local sensitivity differences. In an actual image pickup operation, there are up to several hundred counts per pixel. Local sensitivity differences caused on an individual pixel basis are not greater than statistical errors, and do not incur any serious problem.

When pixel type detectors and a collimator having rectangular holes are positioned with their layout orientations displaced from each other as described above, it is possible to provide a collimator that is capable of avoiding moire patterns and not dependent on positioning accuracy or manufacturing accuracy. In other words, the collimator can be made of low-cost lead so that the manufacturing cost is maintained at a previous level. Further, various collimator hole diameters and depths are selectable in the same manner as before. Consequently, a high degree of versatility results.

To avoid moire patterns, a matched collimator having rectangular holes that match the pixel size may be used. Although the use of such a matched collimator was described earlier, it will now be described in detail. It is said that a matched collimator whose hole positions match the pixel positions (in other words, the septum positions match the detector pixel gap positions) is ideal for use with pixel type detectors, because the sensitivity loss by septa 28 is minimized. However, with the current lead-based collimator, it is difficult to maintain the required manufacturing accuracy in order to make the most of the features of a matched collimator. The reason is that lead is relatively soft and likely to deform. When, for instance, through-holes 27 having a depth of more than 40 mm are manufactured with 0.2 mm thick septa 28 arranged at a pitch of 1.4 mm, it is extremely difficult to position the septa and through-holes within a large collimator measuring 400 mm by 500 mm to an accuracy of 0.05 to 0.1 mm. Even if the mounting positions are slightly displaced, great sensitivity variations may result. Hard tungsten or relatively hard tungsten alloy can be used to manufacture a collimator in order to maintain the required manufacturing accuracy. However, tungsten is an expensive metal and its machining cost is extremely high. Such a solution may work with collimators for use in a small-size gamma camera, but does not provide a practical solution for collimators for use in a normal gamma camera, SPECT, or the like in terms of cost.

Further, the gamma camera rotates or moves in a complicated manner during an image pickup operation. During such a movement, the collimator may deviate from a specified position. Even while the gamma camera is at a standstill for a long period of time, the collimator may gradually deviate from a specified position due to its weight. When displaced, the collimator incurs moire patterns no matter whether a matched collimator is used. This problem can be solved by the embodiment described above.

Figure 14:
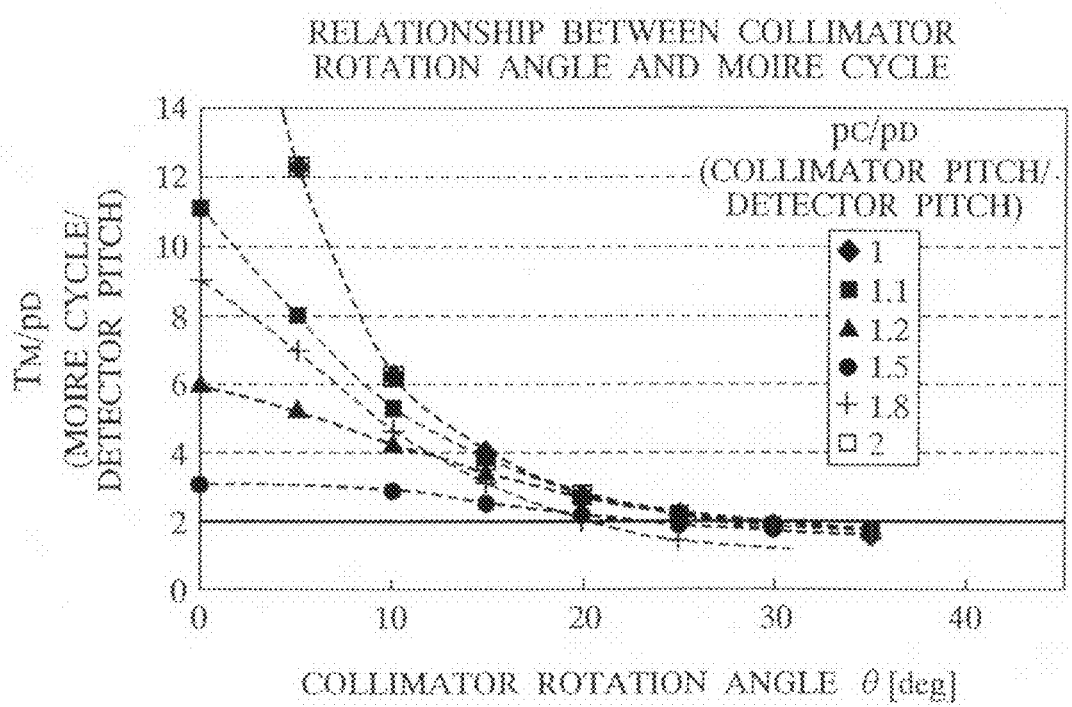
FIG. 14 illustrates the relationship between a collimator rotation angle and moire cycle.

As mentioned earlier, FIG. 12 uses the ratio between a detector pitch of 1 mm and the collimator hole pitch as a parameter and shows the measured ratio between the detector pitch and the moire cycle $T_M$ for the rotation angle θ of the collimator 26. In other words, the geometric similarity rule can be applied to this relationship. When the parameter is $p_c/p_D$ (the ratio of the collimator hole pitch $p_c$ to the detector pitch $p_D$) and rendered dimensionless by the detector pitch $p_D$, the same graphed relationship as indicated in FIG. 12 is obtained as shown in FIG. 14. The moire cycle $T_M$ is the distance between the darkest spot of a moire pattern and the darkest spot of a neighboring moire pattern (or the distance between the lightest spot of a moire pattern and the lightest spot of a neighboring moire pattern). Since moire patterns at rotation angles of 45 deg or greater are the same as for a rotation angle of (90−θ), the maximum rotation angle shown in FIGS. 12 and 14 is 45 deg. In other words, rotation angle symmetry occurs beginning with an angle of 45 deg. Therefore, the same moire patterns are generated at angles of 45°± (45°−θ). Further, when the collimator pitch is more than twice the detector pitch, many pixels are not shaded by the septa 28. Therefore, the shades of the septa 28 are directly projected onto the pixels so that no conspicuous moire patterns are generated. Moire patterns are conspicuous only when the detector pitch is close to the collimator pitch. That is why the maximum collimator pitch shown in FIGS. 12 and 14 is two times the detector pitch. FIGS. 12 and 14 (see FIGS. 10A to 10D and 11A to 11D as needed) indicate that a rotation angle of 30 deg is an angle at which the moire cycle $T_M$/detector pitch $p_D$ is 2.0 or smaller for all collimator pitches according to the present embodiment. In other words, when the rotation angle is 30 deg or greater, moire patterns, which are sensitivity variations occurring at long intervals, disappear at all collimator pitches according to the present embodiment for the reason described later. As regards the relationship between the moire effect and rotation angle, symmetry is achieved at a rotation angle of 45 deg. Therefore, when the rotation angle is between 30 deg (45°−15°) and 60 deg (45°+ 15°), moire patterns disappear at all collimator pitches according to the present embodiment.

When the rotation angle is 20 deg or greater, it can be expected that a moire reduction effect is produced. A good moire reduction effect is produced at collimator pitches of 1.5 mm and 1.8 mm (while the ratio to the detector pitch is 1.5 or 1.8) particularly when the detector pitch is 1 mm. A good moire reduction effect is produced at collimator pitches of 2.1 mm and 2.52 mm when the detector pitch is 1.4 mm, at collimator pitches of 2.4 mm and 2.88 mm when the detector pitch is 1.6 mm, or at collimator pitches of 3.0 mm and 3.6 mm when the detector pitch is 2.0 mm. When the rotation angle is smaller than 20 deg, the influence of moire patterns remarkably increases. As regards the relationship between the moire effect and rotation angle, symmetry is achieved at a rotation angle of 45 deg. Therefore, the result obtained when the rotation angle is 70 deg or smaller is the same as that is obtained when the rotation angle is 20 deg or greater. Consequently, the above statement holds true when the rotation angle is between 20 deg (45°−25°) and 70 deg (45°+25°).

Particularly if the rotation angle is 45 deg, a sensitivity difference arises at intervals of 2 pixels in a situation where the collimator pitch $p_C$ is $\sqrt{2}$ times the detector pitch $p_D$ (the collimator pitch is 1.98 mm when the detector pitch is 1.4 mm, the collimator pitch is 2.26 mm when the detector pitch is 1.6 mm, or the collimator pitch is 2.83 mm when the detector pitch is 2.0 mm). When the resulting periodical position is slightly shifted from the detector center, moire patterns can be mostly removed. Consequently, it is possible to reduce the influence of moire patterns with extreme effectiveness. Even when the cycle is 2 pixels, periodical sensitivity differences can be eliminated with a 3×3 smoothing filter.

It is possible to sufficiently avoid moire patterns at a rotation angle of 20 deg or 70 deg by selecting an appropriate collimator pitch no matter whether it is indicated in FIGS. 12 and 14.

The reason why moire patterns disappear when the moire cycle $T_M$/detector pitch $p_D$ is 2.0 or smaller has already been described with reference to FIG. 12. However, it will now be described in detail. As indicated in FIGS. 10A to 10D and 11A to 11D, moire patterns almost disappear when the moire cycle $T_M$ (see FIG. 10B) is smaller than two times the detector pitch $p_D$ as indicated in FIGS. 12 and 14, that is, at a rotation angle of 30 deg or greater (FIGS. 10C, 10D, 11C, and 11D). When the rotation angle is 35 deg or greater, no measured data is indicated in FIGS. 12 and 14 because the moire cycle $T_M$ could not be measured. To be precise, moire patterns disappear when $T_M \sin \phi$ and $T_M \cos \phi$, which are moire cycles prevailing when oblique moire patterns are projected onto a vertical/horizontal layout, are not more than two times the detector pitch $p_D$, where $T_M$ is the moire cycle and $\phi$ is a moire angle (slightly different from the actual rotation angle $\theta$), which is formed between a moire pattern and the detector 21.

$$(T_M/p_D) \sin \phi \leq 2, (T_M/p_D) \cos \phi \leq 2 \quad \text{(Equation 1)}$$

The minimum cycle for digital imaging is 2 pixels (that is, when pixels having different densities such as black and white pixels are positioned adjacent to each other). Therefore, moire patterns, which are periodical density variations, cannot be recognized on image pixels when the moire cycle $T_M$ for projection onto to the vertical or horizontal pixel layout is not longer than 2 pixels, that is, not more than two times the detector pitch $p_D$. If, for instance, white and black moire patterns are alternately positioned obliquely on screen, white and black moire patterns are also alternately positioned when viewed in the vertical or horizontal direction. The minimum cycle for expressing such density variations is 2 pixels. If the cycle is shorter than 2 pixels, it cannot be expressed on screen (cannot be measured). Since $\sin \phi$ and $\cos \phi$ are smaller than 1, moire patterns are inevitably unrecognizable if $T_M/p_D$ is smaller than 2. This corresponds to a situation where the rotation angle is between 30 deg and 60 deg as described with reference to FIGS. 12 and 14. FIGS. 12 and 14 include values measured in a situation where $T_M/p_D$ is smaller than 2. The reason is that analog overlays shown in FIGS. 10A to 10D and 11A to 11D are used for visual measurements. When actual pixel-based digital images are used, moire patterns are unrecognizable.

Even if $T_M/p_D$ is not smaller than 2, Equation 1 may be satisfied depending on the moire angle $\phi$. The maximum condition for $T_M/p_D$ is $\phi=45°$. In other words, moire patterns may be rendered unrecognizable until $T_M/p_D=2.83$. This is another critical point. In FIGS. 12 and 14, an angle of approximately 20 deg corresponds to the critical point. Near the critical point, Equation 1 may be satisfied depending on the combination of collimator and detector pitches.

However, the sensitivity cannot completely be uniformed by controlling moire patterns. When the collimator pitch is relatively great, the whole area of one pixel is positioned within a through-hole of the collimator 26A' as indicated in FIGS. 11A to 11D so that pixels having the maximum sensitivity locally exist. Meanwhile, the intersection of septa 28A may be positioned over a 1-pixel detector 21 so as to minimize the sensitivity. However, the resulting sensitivity difference is not so periodical. Only a local sensitivity difference arises. In an actual image pickup operation, there are several hundred counts per pixel. Local sensitivity differences caused on an individual pixel basis do not incur any serious problem because they are not greater than statistical errors. Images having increased uniformity can be obtained when a 3×3 smoothing filter is added for post-processing purposes.

As described earlier, two easy-to-use hardware solutions can be applied to control moire patterns. One is the use of a collimator whose hole diameter is less than half the pixel size. The other is the use of a matched collimator having rectangular holes that match the pixel size. Another method is to control moire patterns by performing a post-measurement process, that is, a software process. In this method, a smoothing filter or other diffusion filter is used to make moire patterns inconspicuous. However, moire patterns are sensitivity variations having a long cycle. To make such moire patterns inconspicuous, it is necessary to provide an increased degree of smoothing with a 5×5 matrix smoothing filter or the like. However, the use of a smoothing filter having a great matrix considerably deteriorates the spatial resolution. In practice, therefore, a weighted smoothing filter having a 3×3 matrix, which is the minimum unit of a filter, is used. As described with reference to an after-mentioned comparison example (FIGS. 15A and 15B), the influence of moire patterns remains in a final image when the above-mentioned 3×3 matrix weighted smoothing filter is used.

Figure 15A:
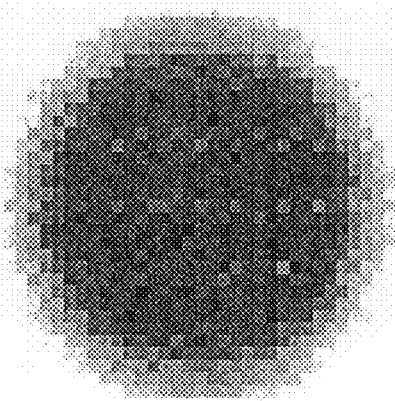
FIGS. 15A and 15B show the image pickup simulation results that are obtained when a conventional hexagonal collimator is used.
Figure 15B:
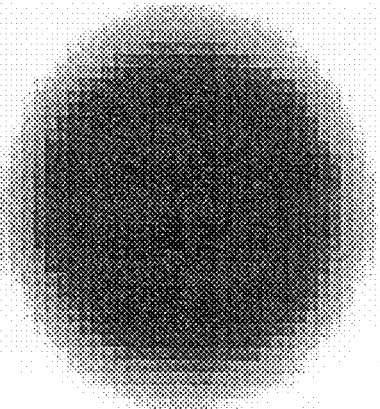
Figure 16A:
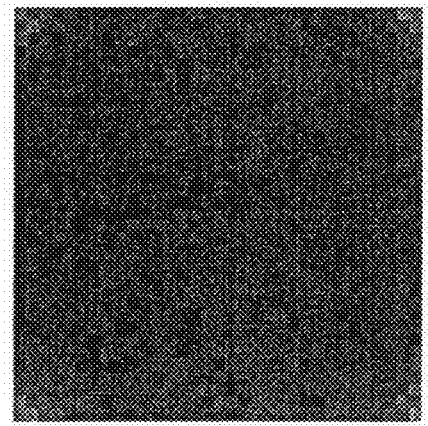
FIGS. 16A and 16B show the image pickup simulation results that are obtained when a rectangular collimator, which is rotated through 45 deg in accordance with one embodiment of the present invention, is used.
Figure 16B:
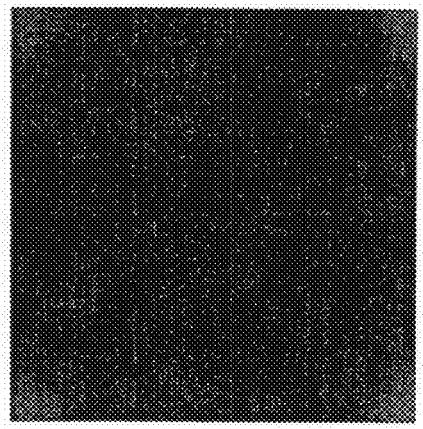

Typical digital images that are actually displayed are shown in FIGS. 15A, 15B, 16A, and 16B. FIGS. 15A and 15B show simulation results that are obtained when a conventional collimator having hexagonal holes is used. FIGS. 16A and 16B show simulation results that are obtained when a collimator having rectangular holes, which are rotated through 45 deg, is used. FIGS. 15A and 15B show calculation results that are obtained in a situation where a hexagonal hole collimator having a side-to-side distance of 1.8 mm, a septum thickness of 0.18 mm, and a length of 39.5 mm is used in relation to a detector pitch of 1.4 mm with the collimator positioned at a distance of 6.8 mm from the detector and a φ40 mm Co-57 planar radiation source positioned at a distance of 100 mm from the collimator. FIGS. 16A and 16B show calculation results that are obtained in a situation where a rectangular hole collimator having a side-to-side distance of 1.8 mm, a septum thickness of 0.18 mm, and a length of 40.0 mm is used in relation to a detector pitch of 1.4 mm with the collimator positioned at a distance of 4.0 mm from the detector and a φ60 mm Co-57 planar radiation source positioned at a distance of 100 mm from the collimator. In FIG. 15A, sensitivity variations having a great periodical structure, that is, moire patterns, are conspicuous. As indicated in FIG. 15B, the moire patterns do not disappear even when a common, 3×3 weighted smoothing filter is used. In FIG. 16A, slight sensitivity variations remain, but sensitivity variations having a long cycle are greatly reduced when compared to moire patterns shown in FIGS. 15A and 15B. This situation can be sufficiently applied to actual use. However, when a 3×3 weighted smoothing filter or the like is used, sensitivity variations are mostly rendered unrecognizable as shown in FIG. 16B.

When a 4×4 smoothing filter, 5×5 smoothing filter, or other large filter is used, it is possible to control moire patterns without resort to the present invention. However, such a large smoothing filter cannot be used under normal conditions because it lowers the spatial resolution.

The present invention uses a 3×3 smoothing filter to shorten the cycle of sensitivity variations having a long cycle, which are recognized as moire patterns, until they cannot be sufficiently recognized. As a result, the present invention can control and uniform moire patterns without significantly impairing the spatial resolution. It goes without saying that the present invention can be used without causing any practical problem even if no filter is used.

As described above, when pixel type detectors and a collimator having rectangular holes are positioned with their layout orientations displaced from each other, it is possible to provide a collimator that fixes a moire problem unique to the pixel type detectors and does not require high positioning accuracy or manufacturing accuracy unlike a matched collimator. In other words, the collimator can be made of low-cost lead so that the manufacturing cost is maintained at a previous level. Further, various collimator hole diameters and depths are selectable in the same manner as before. Consequently, a high degree of versatility results.

Figure 17:
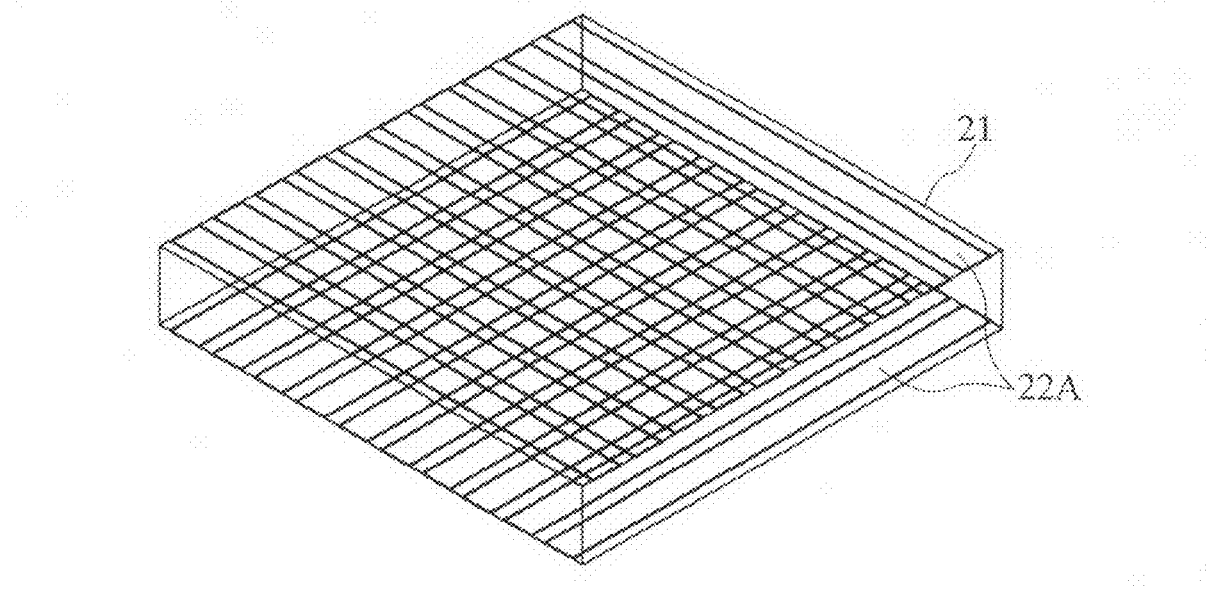
FIG. 17 illustrates still another set of pixel type detectors.

FIGS. 2, 3, 4A, and 4B are used to illustrate detectors and a collimator in conjunction with the foregoing embodiment. FIG. 17 illustrates another example of a pixel type detector. A cross strip type detector may also be used. As indicated in FIG. 17, the cross strip type detector is such that the front and back surfaces of a semiconductor detector are provided with lines of electrodes, which are orthogonal with each other, and that the intersections of electrode lines are regarded as pixels. In the present embodiment, the term "grid pattern" means that vertically arranged detectors 21 and horizontally arranged detectors 21 are orthogonal with each other as shown in FIG. 17. When the example shown in FIG. 17 is taken into consideration, a set of a plurality of rectangular pixels is also counted as a detector.

As described above, the radiation imaging apparatus according to the present invention comprises one or more detectors that read, as a detection signal, the position information about radiation incident on a detector surface that corresponds to the pixel positions and areas of individual image pixels arranged in a grid pattern; a radiation measurement circuit for reading incident radiation information; and a collimator in which a plurality of rectangular through-holes are arranged in a grid pattern and separated by septa. The radiation imaging apparatus acquires the radiation incidence position information about the one or more detectors and generates an image from the acquired information. The collimator, which is included in the radiation imaging apparatus, is rotated through a predetermined angle in relation to the layout of the one or more detectors, which correspond to image pixels, as viewed from above. The radiation imaging apparatus according to the present invention makes it possible to avoid a moire problem, which is unique to pixel type detectors, without requiring high positioning accuracy or manufacturing accuracy unlike a matched collimator.

In the development of a semiconductor-detector-based nuclear medicine diagnosis apparatus, moire patterns make it difficult to obtain practical images with small pixels on the order of 1 mm. The present invention clears a moire problem while considering actual collimator manufacture, and provides a practical radiation imaging apparatus and nuclear medicine diagnosis apparatus that use a semiconductor or pixel type scintillator.

What is claimed is:

1. A radiation imaging apparatus comprising:
   a plurality of rectangular detectors that are arranged in a grid pattern;
   a radiation measurement circuit for reading detection signals of the detectors;
   a collimator in which a plurality of rectangular through-holes are arranged in a grid pattern and separated by septa; and
   a data processing device for acquiring detection signals from the detectors and generating image information,
   wherein the collimator is rotated through a predetermined angle in relation to the layout of the detectors as viewed from above,
   wherein the predetermined angle ranges from 20 deg to 70 deg,
   wherein the collimator pitch is from $\sqrt{2}$ to less than 2.0 times the detector pitch, and
   wherein the data processing device performs a 3×3 matrix smoothing filter process.

2. The radiation imaging apparatus according to claim 1, wherein the predetermined angle ranges from 30 deg to 60 deg.

3. The radiation imaging apparatus according to claim 1, wherein the predetermined angle is 45 deg.

4. The radiation imaging apparatus according to claim 1, wherein the data processing device includes a tomographic information creation device.

5. The radiation imaging apparatus according to claim 1, wherein the collimator is maintained at the predetermined angle during acquiring detection signals from the detectors.

6. A nuclear medicine diagnosis apparatus that uses a radiation imaging apparatus, the radiation imaging apparatus comprising:
   a plurality of rectangular detectors that are arranged in a grid pattern;
   a radiation measurement circuit for reading detection signals of the detectors;
   a collimator in which a plurality of rectangular through-holes are arranged in a grid pattern and separated by septa; and
   a data processing device for acquiring detection signals from the detectors and generating image information,
   wherein the collimator is rotated through a predetermined angle in relation to the layout of the detectors as viewed from above,
   wherein the predetermined angle ranges from 20 deg to 70 deg,
   wherein the collimator pitch is from $\sqrt{2}$ to less than 2.0 times the detector pitch, and
   wherein the data processing device performs a 3×3 matrix smoothing filter process.

7. A radiation imaging apparatus comprising:

pixel type detectors that acquire the position information about radiation incident on image pixels that are arranged in a grid pattern;

a radiation measurement circuit for reading detection signal of the detector;

a collimator in which a plurality of rectangular through-holes are arranged in a grid pattern and separated by septa; and an information creation device for acquiring detection signals from the detectors and generating image information, wherein the collimator is rotated through a predetermined angle in relation to the layout of the detectors as viewed from above, wherein the predetermined angle ranges from 20 deg to 70 deg, wherein the collimator pitch is from $\sqrt{2}$ to less than 2.0 times the detector pitch, and wherein the information creation device performs a 3×3 matrix smoothing filter process.

8. The radiation imaging apparatus according to claim 7, wherein the predetermined angle ranges from 30 deg to 60 deg.

9. The radiation imaging apparatus according to claim 7, wherein the collimator pitch is from $\sqrt{2}$ to less than 1.8 times the detector pitch.

10. The radiation imaging apparatus according to claim 9, wherein the detectors' image pixels that are arranged in a grid pattern are positioned at intervals of 1 mm or longer but shorter than 2 mm.

11. The radiation imaging apparatus according to claim 7, wherein the predetermined angle is 45 deg.

12. The radiation imaging apparatus according to claim 7, wherein the information creation device includes a tomographic information creation device.

13. The radiation imaging apparatus according to claim 7, wherein the collimator is maintained at the predetermined angle during acquiring detection signals from the detectors.

14. A nuclear medicine diagnosis apparatus, comprising:

a radiation imaging apparatus;

a gantry for supporting the radiation imaging apparatus; and a display device for displaying the image information, wherein the radiation imaging apparatus comprises:

pixel type detectors that acquire the position information about radiation incident on image pixels that are arranged in a grid pattern;

a radiation measurement circuit for reading detection signal of the detector;

a collimator in which a plurality of rectangular through-holes are arranged in a grid pattern and separated by septa; and an information creation device for acquiring detection signals from the detectors and generating image information, wherein the collimator is rotated through a predetermined angle in relation to the layout of the detectors as viewed from above, wherein the predetermined angle ranges from 20 deg to 70 deg, wherein the collimator pitch is from $\sqrt{2}$ to less than 2.0 times the detector pitch, and wherein the information creation device performs a 3×3 matrix smoothing filter process.

* * * * *